United States Patent [19]
Kieturakis

[11] Patent Number: 5,787,897
[45] Date of Patent: Aug. 4, 1998

[54] SURGICAL METHOD FOR INTRALUMINALLY PLICATING A FUNDUS OF A PATIENT

[75] Inventor: Maciej J. Kieturakis, San Carlos, Calif.

[73] Assignee: Archimedes Surgical, Inc., Tiberon, Calif.

[21] Appl. No.: 607,415

[22] Filed: Feb. 28, 1996

Related U.S. Application Data

[62] Division of Ser. No. 265,577, Jun. 24, 1994, Pat. No. 5,558,665.

[51] Int. Cl.⁶ .................................................. A61B 1/06
[52] U.S. Cl. ........................... 128/898; 606/1; 600/141; 600/201
[58] Field of Search ................... 606/1, 139–144, 606/191, 192; 600/114–117, 120, 139, 141, 142, 144, 201, 204, 206; 128/898

[56] References Cited

U.S. PATENT DOCUMENTS

| | | |
|---|---|---|
| 936,379 | 10/1909 | Stevens . |
| 2,510,198 | 6/1950 | Tesmer . |
| 3,060,972 | 10/1962 | Sheldon . |
| 3,096,962 | 7/1963 | Meijs . |
| 4,191,191 | 3/1980 | Auburn . |
| 4,535,773 | 8/1985 | Yoon . |
| 4,601,710 | 7/1986 | Moll . |
| 4,654,030 | 3/1987 | Moll et al. . |
| 4,867,404 | 9/1989 | Harrington et al. . |
| 5,116,353 | 5/1992 | Green . |
| 5,147,316 | 9/1992 | Castillenti . |
| 5,147,376 | 9/1992 | Pianetti . |
| 5,179,935 | 1/1993 | Miyagi . |
| 5,201,325 | 4/1993 | McEwen et al. . |
| 5,203,773 | 4/1993 | Green . |
| 5,209,736 | 5/1993 | Stephens et al. . |
| 5,224,952 | 7/1993 | Deniega et al. . |
| 5,226,890 | 7/1993 | Ianniruberto et al. . |
| 5,232,451 | 8/1993 | Freitas et al. . |
| 5,258,003 | 11/1993 | Ciaglia et al. . |
| 5,271,380 | 12/1993 | Riek et al. . |
| 5,279,567 | 1/1994 | Ciaglia et al. . |
| 5,284,130 | 2/1994 | Ratliff . |
| 5,346,504 | 9/1994 | Ortiz et al. .............................. 600/116 |
| 5,368,598 | 11/1994 | Hasson . |
| 5,370,109 | 12/1994 | Cuny . |
| 5,403,326 | 4/1995 | Harrison et al. ......................... 128/898 |
| 5,441,499 | 8/1995 | Fritzsch . |

Primary Examiner—Michael Peffley
Attorney, Agent, or Firm—Skjerven, Morrill, MacPherson, Franklin & Friel LLP; Norman R. Klivans

[57] ABSTRACT

An instrument and method for retracting or repositioning a distal anatomic structure (organ) having a lumen (cavity) by remote manipulation. The method includes advancing the distal end of a flexible variform intraluminal member in a linear shape through a lumen (i.e., the esophagus) in the body to a distal location (the stomach), and deforming the distal end of the instrument to a rigid articulated (arched or curved) shape which retracts tissue surrounding the lumen. Further axial or rotational manipulation of a handle attached to the member correspondingly further retracts the distal anatomic structure to facilitate an endoscopic surgery.

17 Claims, 6 Drawing Sheets

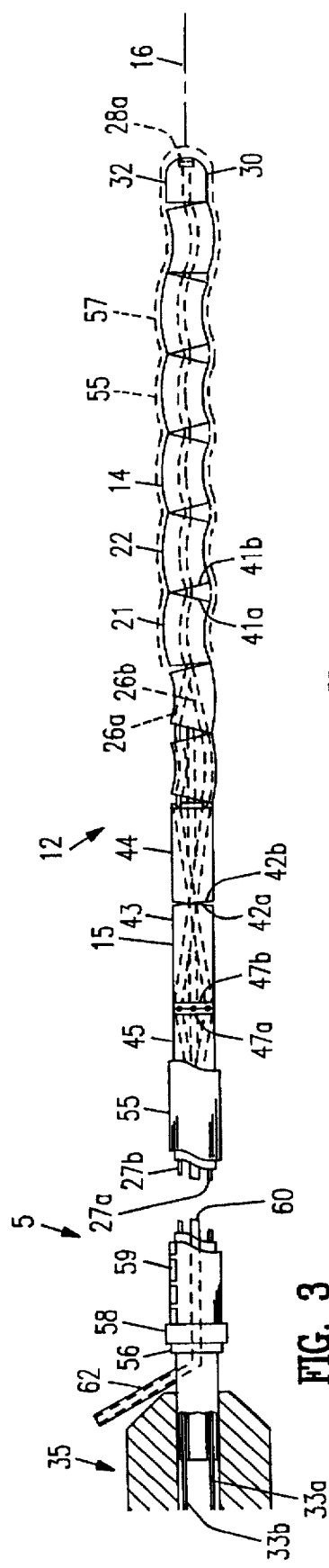
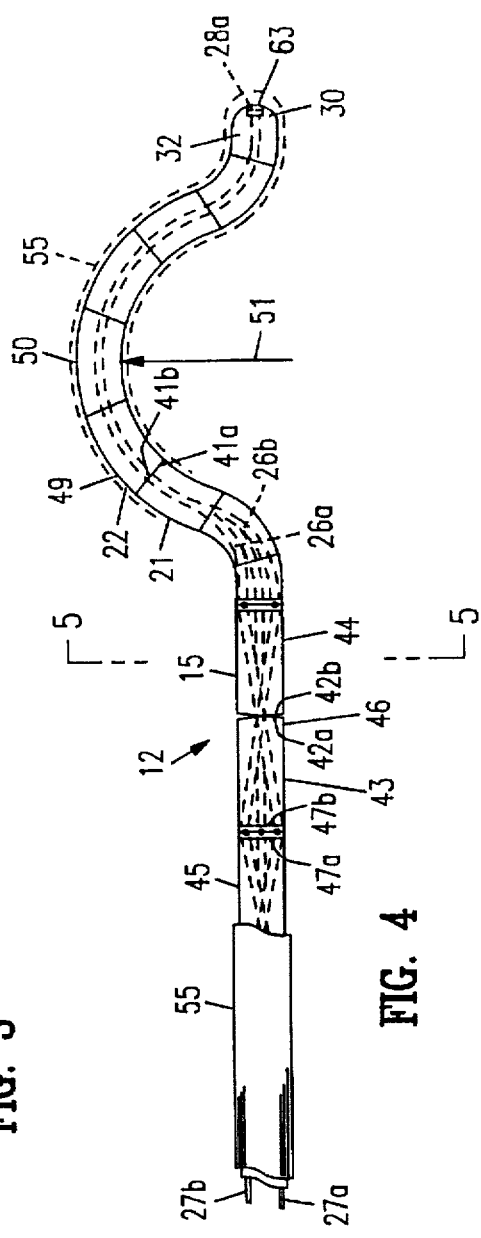
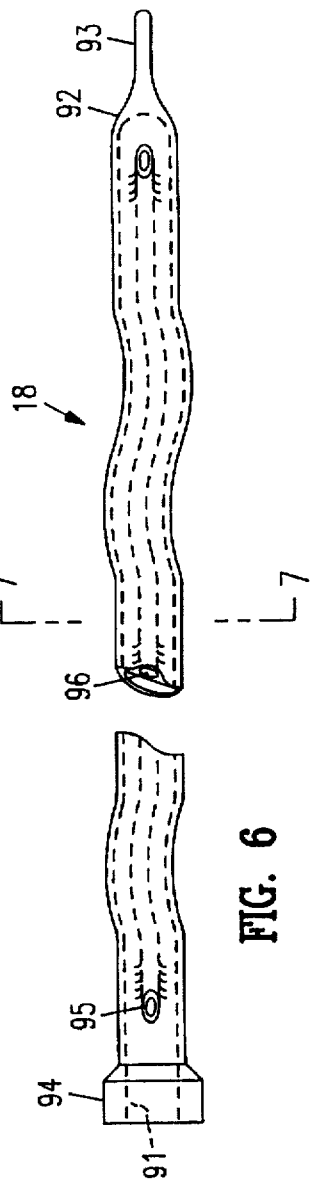
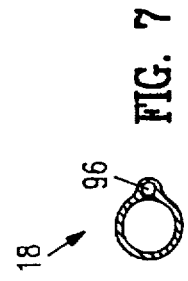
FIG. 3
FIG. 4
FIG. 5
FIG. 6
FIG. 7

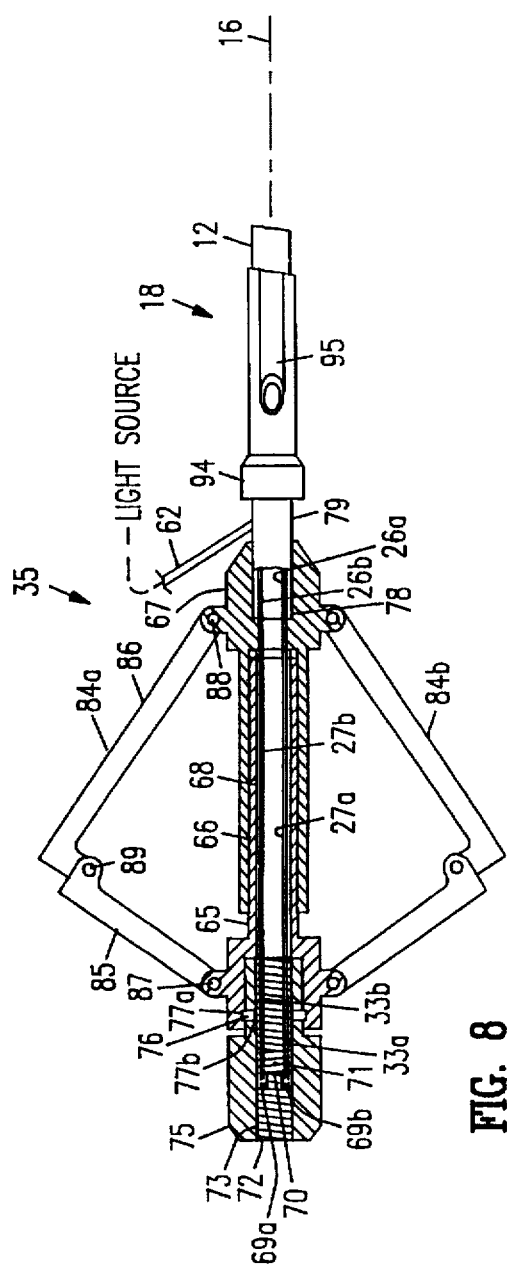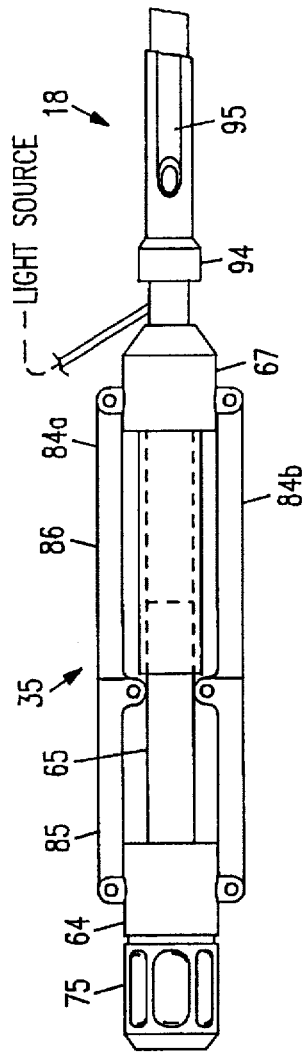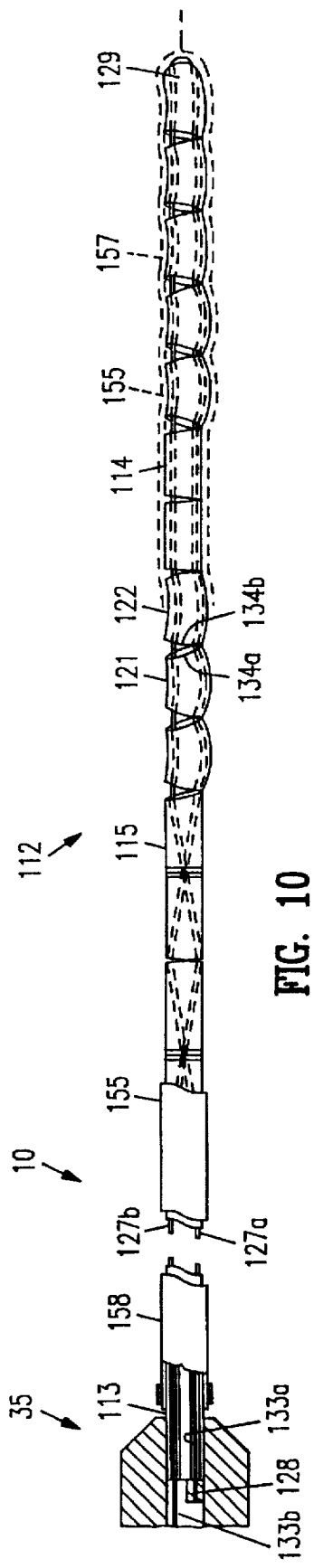

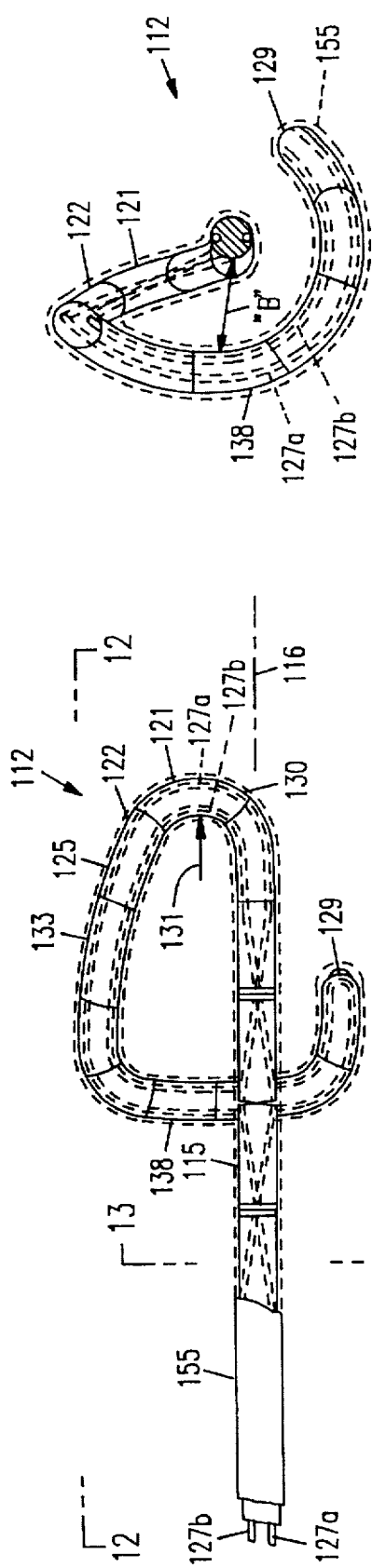
FIG. 11
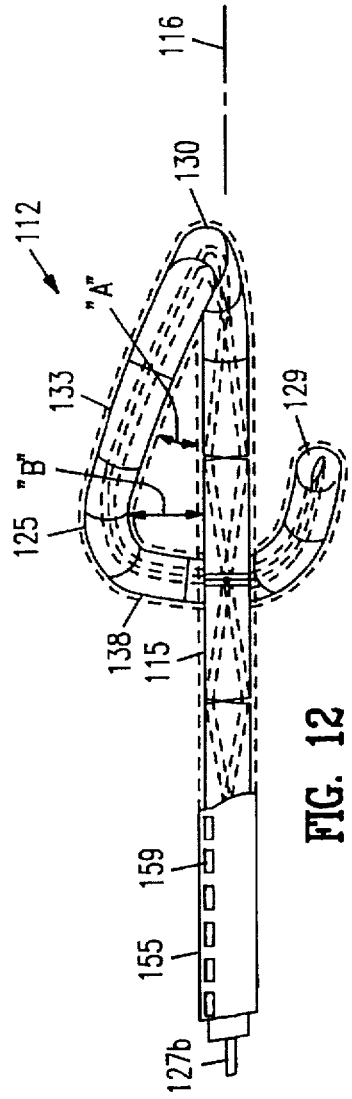
FIG. 12
FIG. 13
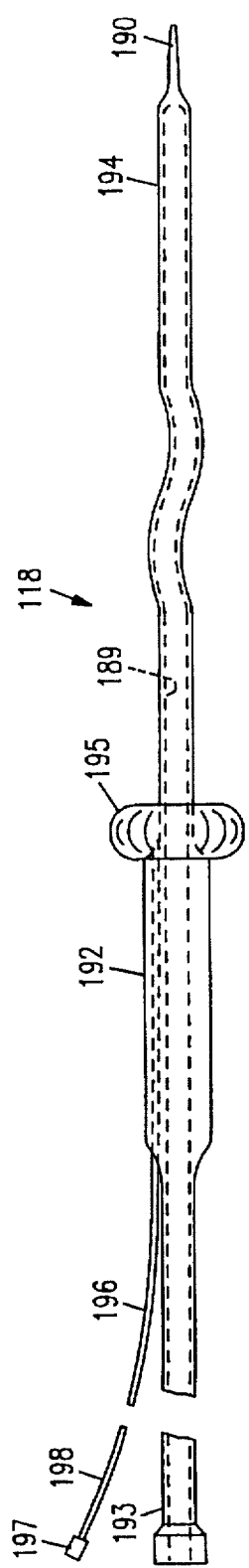
FIG. 14

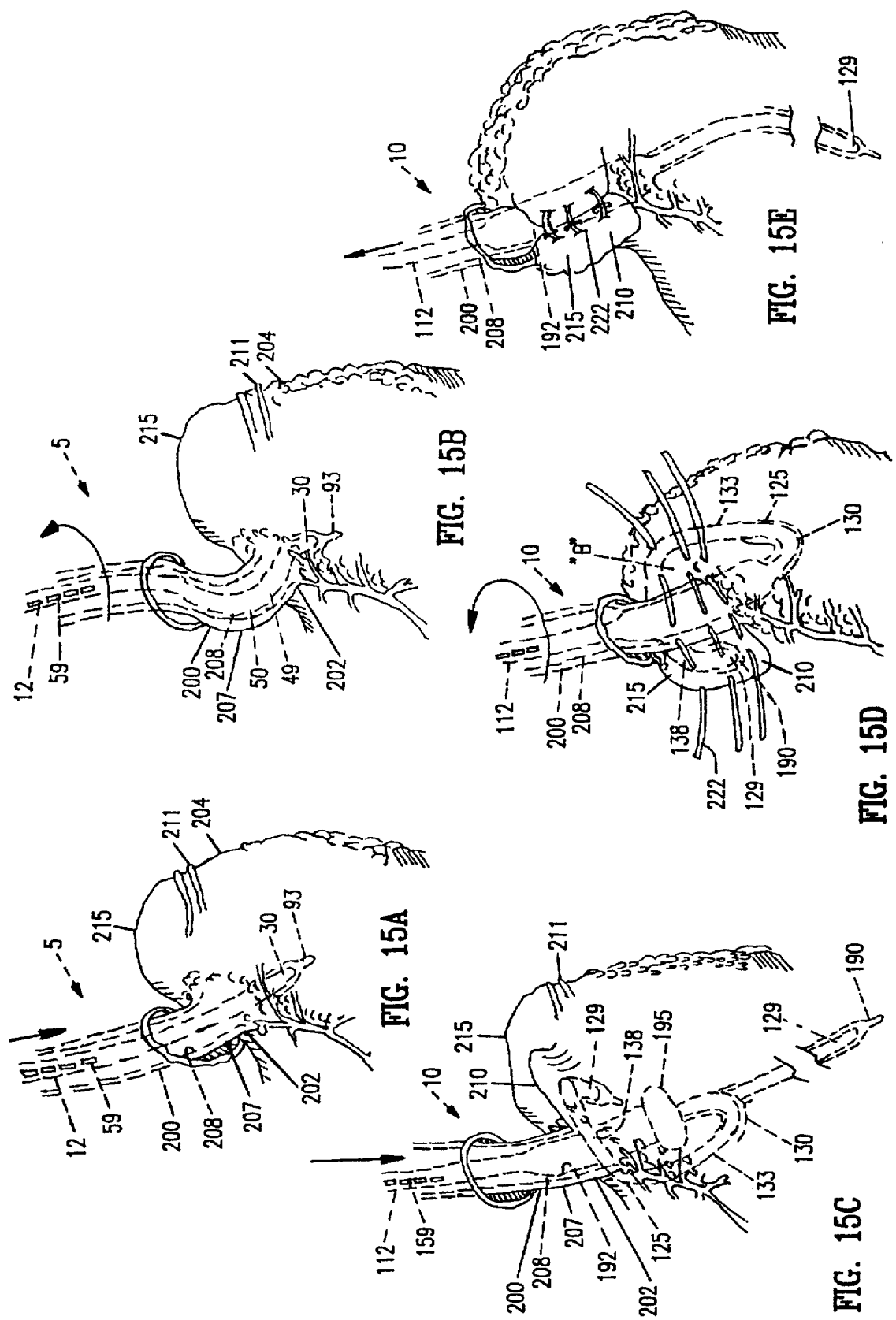

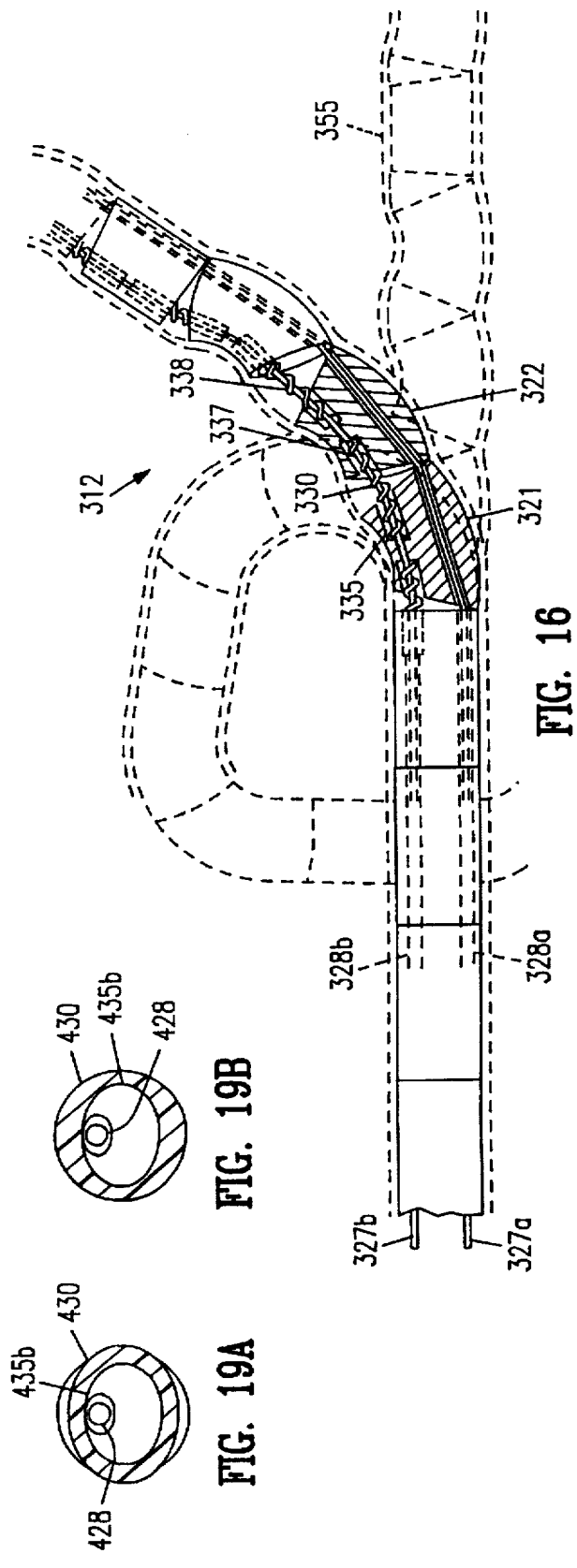
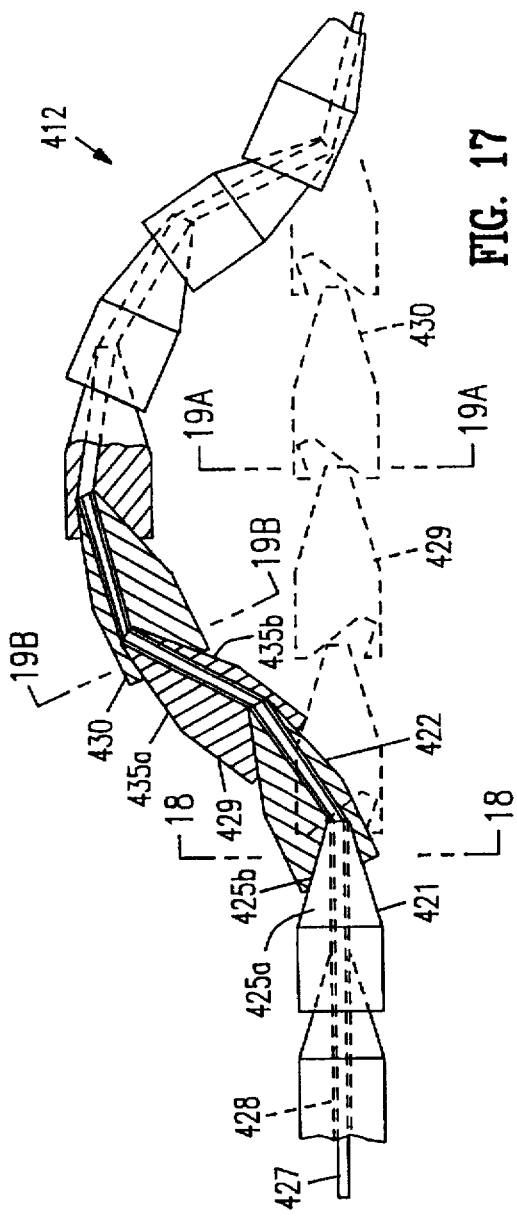
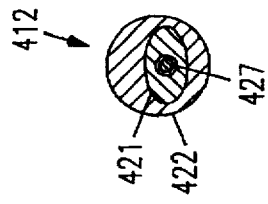

SURGICAL METHOD FOR INTRALUMINALLY PLICATING A FUNDUS OF A PATIENT

This application is a division of application Ser. No. 08/225,577, filed Jun. 24, 1994, U.S. Pat. No. 5,558,665.

BACKGROUND OF THE INVENTION

1. Field of the Invention

This invention relates to surgical instrumentation and more particularly to an instrument and method for retracting or repositioning a distal anatomic structure having a lumen to facilitate an endoscopic surgery.

2. Description of the Prior Art

In a "minimally invasive" endoscopic surgery, for example in an insufflated abdominal cavity, dissection, cutting and suturing are performed with various elongate instruments introduced into the interior of the body through cannulas. It has been found that some endoscopic procedures are complex and time-consuming because of difficulties in retracting or repositioning organs or structures with an elongate instrument (e.g., a grasper). Since all such instruments are introduced through cannulas (tubes) which are in stationary positions, it often is difficult to lift, rotate, reposition or otherwise retract an anatomic structure to access the site of the actual procedure. On occasion, the retracting instruments have to cross the region of dissection, obstructing the surgeon's view and interfering with the dissecting instruments.

An illustrative example of a procedure that is difficult to perform endoscopically is a gastric wrap (e.g., a "Nissen fundoplication") for alleviating gastroesophageal reflux. In such a fundoplication, the surgeon develops a fold or plication in the fundus of the stomach and then wraps and sutures the plication generally around the gastroesophageal junction. To accomplish the procedure endoscopically, the surgeon must mobilize the esophagus and fundus by dissecting connective tissues behind the structures, then grasp the exterior of the fundus and drag it behind and around the esophagus, then suture the plication in place. Such retraction procedures are difficult to accomplish with conventional endoscopic graspers. An open surgery to accomplish a fundoplication is undesirable because it requires lengthy postoperative recuperation and also requires a long disfiguring upper abdominal incision. There is therefore a need for new instruments and methods for retracting or repositioning anatomic structures in a "minimally invasive" surgery and particularly for accomplishing the retraction of the esophagus and fundus in an endoscopic anti-reflux procedure.

SUMMARY OF THE INVENTION

In general, the instrument of the present invention includes an elongate variform intraluminal member having a substantially flexible primary linear shape that is capable of being deformed into a substantially rigid non-linear secondary shape. The variform member is introduced in its linear shape into a lumen (cavity) in an anatomic structure in the body in a proximal location in the primary shape, then advanced to a distal location within the lumen and thereafter deformed or articulated into the rigid secondary shape. The deformation of the variform member into the predetermined secondary shape retracts or repositions tissue surrounding the lumen. Further manipulation of a proximal handle of the instrument further repositions tissue.

In an exemplary method, assume that the surgeon wishes to retract or reposition the fundus of the stomach in an endoscopic Nissen fundoplication. Two variform intraluminal retractors are utilized. Both retractors are flexible in a primary shape for introduction into the patient's esophagus and stomach. Both retractors have a distal region that is deformable into a rigid secondary shape by actuation of deforming means at a proximal handle location. The esophageal retractor has a "C"-shape and is utilized to arch the esophagus and thus mobilize the distal esophageal region. The fundus retractor has a distal loop in the secondary shape that resembles the loop in a "pig's tail." The distal loop along with a radially-projecting tip are adapted to reach around and above the gastroesophageal junction and to exert forces on the fundus to cause its transposition as the instrument is rotated about its axis. Such rotation of the retractor plicates the fundus wall and thereafter rotates the plication up to 360° around the esophagus so it can be approximated with sutures or other adjoining means to the anterior aspect of the fundus which remains in its unretracted anatomical position.

In general, the present invention provides an instrument and method utilized in an endoscopic surgery for retracting a distal anatomic structure having a lumen, i.e., a hollow viscus (organ). The present invention also provides an instrument having a variform intraluminal member capable of a flexible shape for introduction through a lumen in a viscus and a rigid articulated shape for repositioning the viscus intraluminally. The present invention also provides an instrument and method in which such intraluminal retraction is accomplished by manipulation of the instrument from a proximal location.

The present invention also provides an instrument and method for an anti-reflux or gastric wrap procedure in which an intraluminal retractor plicates the region of tissue in the fundus of a human stomach which has the least resistance to such retraction (i.e., most mobile tissue) to provide the most physiologically desirable wrap. The present invention also provides an instrument and method which allows for transpositioning the wall of the fundus around the esophagus in a manner which makes it unnecessary to divide short gastric vessels. The present invention also provides an instrument and method for retracting a human esophagus in a manner making it unnecessary to grasp the exterior of the esophagus with a grasping instrument.

The present invention also provides an instrument and method of the above character in which the variform intraluminal member carries a fiberoptic light means to transilluminate tissue for locating the region of the instrument that is marked by the light. The present invention also provides an instrument and method in which the distal end of the intraluminal member has a pliable tip for leading the instrument through a lumen. The present invention also provides an instrument and method in which the intraluminal member incorporates a working channel to accommodate an endoscope, an accessory instrument or for therapeutic agent delivery or suction. Additional advantages and features of the invention appear in the following description in which several embodiments are set forth.

BRIEF DESCRIPTION OF THE DRAWINGS

FIG. 3 is an elevational view of a portion of the device of FIG. 1.

FIG. 4 is an elevational view of a portion of the device of FIG. 1 taken along line 4—4 of FIG. 1 rotated 90°.

3

Figure 1:
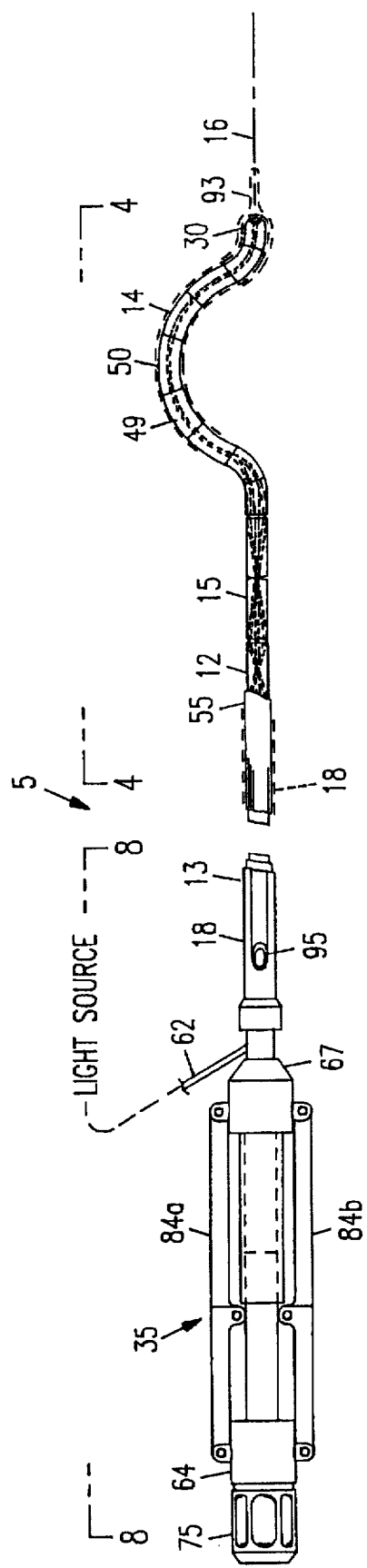
FIG. 1 is an elevational view of a first embodiment of the present invention in a certain position.

FIG. 5 is an elevational view of the portion of the device of FIG. 1 taken along line 5—5 of FIG. 4 rotated 90°.

FIG. 6 is an elevational view of disposable sheath used in conjunction with the device of FIGS. 3–5.

FIG. 7 is a sectional view of the sheath of FIG. 6 taken along line 7—7 of FIG. 1 rotated 90°.

FIG. 8 is a partial sectional view of a portion of the device of FIG. 1 in a first position taken along line 8—8 of FIG. 1 rotated 90°.

FIG. 9 is an elevational view of the portion of the device in FIG. 8 in a second position.

Figure 2:
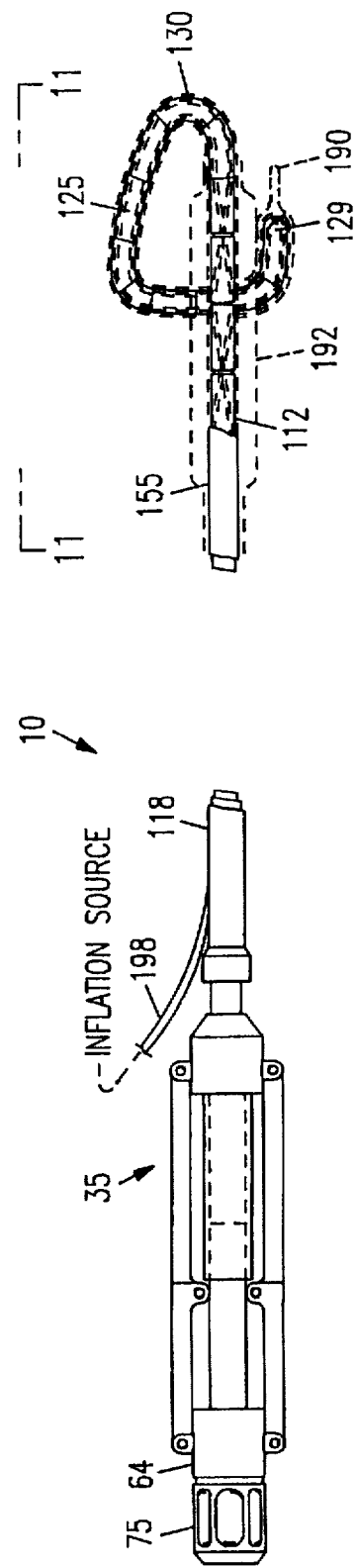
FIG. 2 is an elevational view of a second embodiment of the present invention in a certain position.

FIG. 10 is an elevational view of a portion of the device of FIG. 2.

FIG. 11 is an elevational view of the portion of the device of FIG. 2 taken along line 11—11 of FIG. 2 rotated 90°.

FIG. 12 is an elevational view of the device taken along line 12—12 of FIG. 11.

FIG. 13 is transverse sectional view of the device taken along line 13—13 of FIG. 11.

FIG. 14 is an elevational view of disposable sheath used in conjunction with the device of FIGS. 10–13.

FIGS. 15A–15E are schematic illustrations showing the manner in which the method of the present invention is practiced utilizing the instruments of FIGS. 1 and 2.

FIG. 16 is a partial sectional view of a portion of an alternative variform intraluminal member.

FIG. 17 is a partial sectional view of a portion of an alternative variform intraluminal member.

FIG. 8 is a transverse sectional view of the variform member of FIG. 17 taken along line 18—18 of FIG. 17 rotated 90°.

FIG. 19–19B are alternative transverse sectional views of the variform member of FIG. 17 taken along lines 19A—19A and 19B—19B of FIG. 17 rotated 90°.

DESCRIPTION OF PREFERRED
EMBODIMENTS OF THE INVENTION

By way of example, FIGS. 1 and 2 depict the variform intraluminal retractors to be employed in an endoscopic Nissen fundoplication. Esophageal retractor 5 illustrated in FIG. 1 is adapted for retracting or repositioning the esophagus and is shown in an articulated or secondary shape. Fundus retractor 10 illustrated in FIG. 2 is adapted for repositioning the fundus of the stomach and is shown in an articulated or secondary shape.

More in particular, esophageal retractor 5 has variform intraluninal member 12 with proximal (near) and distal (far) regions respectively 13 and 14 and medial (middle) region 15. Referring to FIGS. 3–5, intraluminal member 12 has a generally cylindrical shape along longitudinal axis 16 with an overall length of approximately 500 millimeters. The cross-sectional dimension of intraluminal member 12 when assembled with disposable sheath 18 (see FIGS. 6–7), further described below, would range in diameters from #20 to #60 French for various patients.

Articulating retractor 5 is deformable to a rigid articulated or secondary shape (see FIGS. 1 and 4–5). from the primary (straight) shape (see FIG. 3). Referring to FIG. 3, variform intraluminal member 12 includes an interior assembly of longitudinal articulating elements, for example elements 21 and 22, that are made of any suitable material such as metal or plastic. Longitudinal bores 26a and 26b extend through each articulating element in substantial alignment. FIG. 5 illustrates a transverse sectional view of an articulating

4 element. A tensioning member with longitudinal-extending portions 27a and 27b is made of flexible braided stainless steel cable or another suitable material and extends through bores 26a and 26b. The distal ends of members 27a and 27b are fixed with crimp nuts 28a and 28b (not visible) in tip 30 of distalmost articulating element 32. Proximal ends 33a and 33b of the tensioning members are secured in handle assembly 35 as described below (see FIGS. 1 and 8–9). In FIG. 3, the tensioning member portions are shown in a relaxed or non-tensioned position thus configuring intraluminal member 12 in the non-articulated flexible or primary shape. In FIGS. 4–5, the tensioning member portions are shown in a tensioned position configuring intraluminal member 12 in the rigid articulated or secondary shape.

As illustrated in FIGS. 3 and 4, the proximal planar abutment face 41a of articulating element 21 is angled with respect to axis 16 and abuts similarly angled distal planar abutment face 41b of articulating element 22. When tensioning members 27a and 27b are in a tensioned position as in FIG. 4, abutment faces 41a and 41b are in contact and form a substantially rigid interface between articulating elements 21 and 22. In medial region 15 of intraluminal member 12, the abutment faces 42a and 42b of adjacent articulating elements, for example 43 and 44, have a convex form when viewed in side elevation. When the tensioning member is in a tensioned position as in FIG. 4, convex abutment faces 42a and 42b are in contact and form a semi-rigid hinge connection 46 between the articulating elements 43 and 44. Adjacent semi-rigid hinge connection 45 results from similar convex abutment faces 47a and 47b except rotated 90° (or another radial angle) along with tensioning portions 27a and 27b. Thus, medial region 15 in intraluminal member 12 is flexible yet rotational forces applied to handle assembly 35 and proximal region 13 are carried to the distal region 14.

The shape of distal region 14 of intraluminal member 12 in the articulated or secondary shape exhibits a "C"-shape 49 with distalmost tip 30 extending substantially straight along axis 16. The "C"-shape 49 has apex 50 illustrated with a radius 51 of approximately 60 mm. in FIG. 4 but such radius may range from 30 mm. to 200 mm. and is not limiting.

Outer jacket 55 with proximal and distal ends, 56 and 57, is made of any suitable flexible material, for example a thin wall elastomeric tubing such Tygon® R-1000. Jacket 55 may alternatively be fabricated of thin wall plastic such as PTFE® of FEP® that is flexible by buckling slightly. When the articulating elements are in a non-tensioned position (see FIG. 3), jacket 55 assists in straightening medial region 15 and distal region 14 of intraluminal member 12 to help the axial forces applied to handle assembly 35 generally along longitudinal axis 16 to assist in pushing intraluminal member 12 though the patient's esophagus. Jacket 55 is fixed over member 12 by metal band 58 compressed over the jacket. Jacket 55 has indicator stripe 59 extending along the length of intraluminal member 12 for reasons explained hereinbelow. Optic fiber 60 is incorporated into central bore 61 in intraluminal member 12. A light source is connected to proximal end 62 of optic fiber 60 for reasons explained below. The distal end 63 of optic fiber 60 terminates at distalmost articulating element 32.

Referring to FIGS. 8–9, handle assembly 35 is generally cylindrical in shape and is suitable for grasping by the human hand. Proximal handle 64 has reduced diameter cylinder portion 65 that telescopes in primary axial bore 66 in distal handle 67 (see FIGS. 8 and 9). Proximal handle 64 has longitudinal bore 68 that is aligned with bores 26a and 26b in the articulating elements and tension member portions 27a and 27b extend therethrough. The proximal ends, 33 and 33b of the tensioning member have crimp nuts 69a and 69b crimped over said ends and abut the proximal face 70 of threaded adjustment nut 71. Nut 71 is disposed in female threads 72 within bore 73 of adjustment grip 75. Grip 75 is maintained in axial relation to proximal handle 64 by lock ring 76 disposed in cooperating annular grooves 77a and 77b in handle 64 and grip 75. Distal handle 67 has secondary bore 78 with proximalmost articulating element 79 fixed therein with adhesives or other suitable means.

A pair of opposing squeeze grips 84a and 84b are adapted to reciprocate proximal handle 64 relative to distal handle 67 in order to tension the tensioning member. Proximal and distal tensioning lever arms respectively 85 and 86 pivot around proximal pins 87 and distal pin 88 as well as intermediate pin 89. Inwardly directed force on the opposing squeeze grips 84a and 84b directed toward axis 16 telescopes cylinder 65 of handle 64 proximally from within axial bore 66 in distal handle 67 to pull the tensioning member portions proximally (see FIG. 9). Rotation of adjustment grip 75 adjusts the overall length of the tensioning member with respect to handle assembly 35 and the plurality of articulating elements.

FIGS. 6–7 depict disposable sheath 18 that is adapted to be slipped over intraluminal member 12. Sheath 18 is made of transparent flexible material such latex and has open proximal end 91 and closed distal end 92 with very flexible tapered tip 93. As noted above, the outer diameter of sheath 18 would be manufactured in several sizes ranging from #20 to #60 French for different size esophageal lumens. Gripping collar 94 molded into sheath 18 is adapted for grasping with the fingers to pull the sheath over intraluminal member 12. Flexible working channel 95 with interior lumen 96 is incorporated into sheath 18. The diameter of lumen 96 may be any be any suitable dimension, for example from 0.6 to 3 millimeters or more, to accommodate a flexible shaft accessory instrument (e.g., an endoscope or forceps). Working channel 95 also may be utilized to deliver therapeutic agents to the patient's stomach or to suction air or liquid secretions from the stomach.

Referring now to FIGS. 1 and 10–13, the other intraluminal retraction instrument necessary for a fundoplication is fundus retractor 10 shown with intraluminal member 112 having proximal and distal regions respectively 113 and 114 and medial region 115. Retractor 10 includes the handle assembly 35 of the first-described retractor 5. Fundus retractor 10 is deformable between a flexible linear or primary shape along axis 116 (see FIG. 10) and a rigid articulated or secondary shape (see FIGS. 11–13).

Fundus retractor 10 principally differs from esophageal retractor 5 in its articulated or secondary shape and in its cross-sectional dimensions. Intraluminal member 112 has proximal and distal regions 113 and 114 and medial region 115. Intraluminal member 112 has a generally tubular shape along longitudinal axis 116 with an overall length of approximately 800 millimeters. The diameter of member 112 is dimensioned to cooperate with disposable sheath 118 (see FIG. 14).

Intraluminal member 112 is made of an interior assembly of articulating elements, for example elements 121 and 122, that is similar to previously-described retractor 5. The distal region 114 may be deformed into a loop 125 in its secondary shape. Tensioning member 127 is made up of portions 127a and 127b that extend in a loop around tip 129. One proximal end 133a of portion 127a is fixed with crimp nut 128 in the proximalmost articulating element (see FIG. 10). The other proximal end 133b of tension member portion 127b is tensioned by actuation of the squeeze grips in handle assembly 35 as described above. It is only necessary to tension portion 127b to articulate the intraluminal member into the secondary shape. The variously angled abutment faces, for example 134a and 134b, cause intraluminal member 112 to deform into loop 125 in a compound curved shape.

The distal region of intraluminal member 112 may take on varied shapes to accomplish its function of retracting the fundus, with such shapes generally exhibiting a distal curve shape with a tip projecting outward from the axis of the instrument proximal to (above) the distal curve. In one preferred embodiment shown in FIG. 11, the shape of distal end 114 of intraluminal member 112 in the secondary shape is complex and generally resembles the loop of a "pig's-tail" with loop 125 terminating in tip 129. Viewed in side elevation (see FIG. 11), loop 125 may turn from 200° to 360° from axis 116 until intraluminal member 112 crosses itself. In such side elevational view, loop 125 has a distal curve portion 130 with radius 131 dimensioned from 10 to 25 millimeters and a proximally-extending portion 133 extending from 0 to 40 millimeters, but such dimensions are not limiting.

In an elevational view from above as in FIG. 12, it will be noted that loop 125 is skewed from axis 116 by angle "A" that may range from 5° to 40°. FIG. 12 further illustrates that angle "A" provides gap "B" ranging from 5 to 30 millimeters where intraluminal member 110 crosses itself for reasons described hereinbelow, with such dimensions not limiting. When viewed in transverse sectional view as in FIG. 13, the termination portion 138 of loop 125 may curve around axis 116 and the medial region 115 of intraluminal member 112 from 0° to 180° with gap "B" in another view ranging from 5 to 30 millimeters. Tip 129 is adapted to project radially around or somewhat outwardly with respect to axis 116.

Outer jacket 155 with proximal and distal ends respectively 156 and 157 is made of any suitable flexible material as described in conjunction with retractor 5 above. Indicator stripe 159 in included on jacket 155 for reasons described below (see FIG. 12).

FIG. 14 depicts an elevational view of elongate disposable sheath 118 with a central passageway 189 that is dimensioned to slide over intraluminal member 112 and is made of suitably flexible material such as latex. The distalmost tip 190 is tapered and made of very flexible material. The outer diameter of the medial region 192 of sheath 118 is illustrated in diameter #50 French but would be manufactured in diameters ranging from #40 to #60 French for different patients with different size esophaguses and for different gauge gastric wraps. The proximal and distal regions respectively 193 and 194 of the sheath have thin walls.

Inflatable collar 195 capable of collapsed and inflated conditions is depicted in FIG. 14 in an inflated condition. Collar 195 is incorporated into sheath 118 in medial region 192 with inflation tube 196 extending to a proximal location along handle assembly 35. Collar 195 is preferably made of elastomeric material, for example latex, and is inflatable to a diameter of approximately 40 to 50 millimeters. A Luer-type fitting 197 at the proximal end 198 of tube 196 is adapted for cooperating with an inflation source supplying an inflation medium, for example air or saline solution from a syringe (not shown).

Operation and use of the instruments shown in FIGS. 1 and 2 in performing the method of the present invention is described briefly as follows. Assume that the surgeon is to perform an endoscopic Nissen fundoplication, although the device may be used in an open surgical procedure. The surgeon prepares the patient with a suitable anesthesia, insufflates the abdominal cavity and places three or more cannula assemblies through the abdominal wall, for example using the safety heliscopic cutter disclosed in co-pending patent application Ser. No. 08/187,753 filed Jan. 26, 1994 and the "inside-out" trocar disclosed in a co-pending and commonly invented patent application Ser. No. 08/255,273, [docket No. M-2890], filed Jun. 1, 1994 entitled "Instrument and Method for Performing Surgery Around a Viewing Space in the Interior of the Body" both incorporated by reference. The surgeon then utilizes an endoscope to view the interior of the body in the region of the gastroesophageal or GE-junction and stomach.

Both retractors 5 and 10 are prepared by placing disposable sheaths 18 and 118 over the variform intraluminal members respectively 12 and 112 of each retractor. The surgeon's assistant then grasps retractor 5 and configures variform member 12 in the primary shape by opening squeeze grips 84a and 84b outwardly from axis 16 (see FIG. 3) so that the medial region 15 and distal region 14 of intraluminal member 12 are substantially straight and flexible. The assistant introduces tip 30 with flexible tip 93 of sheath 18 through the patient's mouth into esophagus 200 and advances intraluminal member 12 distally until tip 30 is in the region of GE-junction 202 or slightly within stomach 204 (see FIG. 15A). A light source connected to optic fiber 60 emits a light through tip 30 of intraluminal member 12. The surgeon can see a spot of light through the translucent tissue of the esophagus to locate the tip of the instrument. It should be appreciated that the light may be emitted from any appropriate point within the distal region 14 of the intraluminal member to function as a locator.

The assistant turns the instrument to a correct angle by reference to indicator stripe 59 which can be seen through transparent sheath 18 and is in angular registration with distalmost tip 30 such that apex 50 of "C"-shape 49 is disposed toward the front of the patient's body (see FIG. 15B). While the surgeon views the distal esophagus 207 endoscopically, the assistant applies pressure on squeeze grips, 84a and 84b, directed toward axis 116 which pulls the distal ends 33a and 33b of the tensioning member proximally and deforms the articulating elements of intraluminal member 12 into the articulated or secondary shape (see FIG. 15B).

The diameter of retractor 5 fits somewhat loosely in esophageal lumen 208 and the articulation of retractor 5 causes the exterior of esophagus 200 to assume the "C"-shape 49 of the retractor. Such retraction causes esophagus 200 to arch outwardly above GE-junction 202 thus retracting and mobilizing the distal esophagus 207 by stretching and dissecting connective tissues. The surgeon's assistant may rotate retractor 5 and "C"-shape 49 in an arc of approximately 90° to 180° to further dissect connective tissues. Thereafter, the surgeon may easily dissect remaining connective tissues intact behind the mobilized esophagus with an accessory instrument (e.g., a grasper). Thereafter, the assistant opens squeeze grips, 84a and 84b, outwardly from axis 116 (see FIGS. 7-8) to return intraluminal member 12 to its primary shape and withdraws the retractor 5 from esophagus 200.

During the procedure, working channel 95 incorporated into disposable sheath 18 may be used to introduce a fiberscope or other accessory instruments into the stomach. Alternatively, the working channel may be used to suction air or secretions from the stomach or to deliver therapeutic agents.

The surgeon's assistant next grasps fundus retractor 10 in its straight and flexible or primary shape (see FIG. 10) and introduces intraluminal member 112 into the patient's esophagus 200 and stomach (via his mouth) 204 as shown in an alternative phantom view in FIG. 15C. The assistant then inflates inflatable collar 195 with an inflation medium, for example air or saline solution from a syringe (not shown). Collar 195 is sufficiently large to prevent it from passing through GE-junction 202 as the intraluminal member 112 is moved proximally. The assistant then adjusts retractor 10 to the correct radial angular position by rotating the retractor 10 until indicator stripe 159 is facing the front of the patient's body. The assistant then applies inward pressure on the squeeze grips in handle 35 to articulate the distal end 114 of intraluminal member 112 to the looped or secondary shape (see FIGS. 10–13). In an alternative phantom view in FIG. 15C, retractor 10 is articulated to the secondary shape at which time the surgeon endoscopically can view the wall of fundus 215 "tenting" outwardly as tip 129 and terminal region 138 exert forces on the wall and begin repositioning the fundus.

The particular secondary shape of distal region 114 of the instrument is adapted to accomplish several objectives (see FIGS. 11–13). The distalmost loop portion 130 is adapted to extend through esophagus 200 and generally curve closely around GE-junction 202 with the said junction fitting into gap "B" (see FIG. 12–13). The diameter of medial region 192 of sheath 118 is selected to gauge the diameter of the gastric wrap. The medial region 192 fits snugly inside esophageal lumen 208 and GE-junction 202 to intraluminally support the lumen as plication 210 is rotated around the esophagus and approximated.

Intraluminal retraction or repositioning of the fundus 215 offers a very important advantage over currently practiced methods which retract the fundus typically by grasping and pulling on its exterior wall. In such current practice, it is necessary to ligate and divide one or more short gastric vessels 211 (see FIG. 15A) between the spleen and stomach in order to mobilize the fundus for wrapping around the esophagus. In contrast, in an intraluminal retraction with instrument 10, it should not be necessary to divide any short gastric vessels to accomplish the fundoplication. The proximally-extending portion 133 of loop 125 is adapted to reach proximally well above GE-junction 202 and tip 129 and terminal portion 138 thus engage the softest tissue in the inner wall of fundus 215. Proximal and rotation forces on the instrument may cause tip 129 and terminal portion 138 to slip at first until loop 125 encounters the most pliable tissue of the fundus which then plicates easily. In this manner of utilizing the instrument, only the least resistant (most mobile) tissue plicates which is physiologically desirable. The more resistant tissue of the fundus, including tissue which is overlain with a gastric artery 211, typically should resist plicating and such tissue will remain unretracted thus making it unnecessary to divide a short gastric vessel.

FIG. 15C depicts intraluminal member 112 in a somewhat distal position after being deformed to the secondary position. The surgeon instructs the assistant to lift intraluminal member 112 to a more proximal position until balloon 195 abuts the GE-junction. Thereafter, the assistant rotates handle assembly 35 and intraluminal member 112 counterclockwise while the surgeon endoscopically views the wall of fundus 215 tenting further and then developing plication 210. The assistant continues counterclockwise rotation until plication 210 is retracted and wrapped around distal esophagus 207 as shown in FIG. 15D. In FIG. 15D, note that tip 190 of sheath 118 is sufficiently flexible to bend over and play no role in the plication of tissue. The compound radiuses around loop 125 are adapted to overcome counterforces caused by the fundus' resistance to rotation. Such counterforces are generally opposed by directing all rotational forces applied to handle assembly 35 along the continuously curved axis of intraluminal member 112.

When plication 210 is in the desired location as shown in FIG. 15D, the surgeon places several sutures 222 through the plication, distal esophagus 207 and fundus 215. FIG. 15E depicts a completed fundoplication with the instrument in phantom view reconfigured to its primary shape for withdrawal from the esophagus.

It should be appreciated that fundus retractor 10 may be provided with a fiber optic light source as in esophagus retractor 5, although not so described herein.

FIG. 16 depicts a partial sectional view of an alternative embodiment of a variform intraluminal member 312 with "sequential" deforming means for use with any intraluminal retractor. The variform member 312 shows representative articulating elements 321 and 322 in a deforming position between the primary and secondary shapes (shown in phantom view). Tensioning members 327a and 327b are slidably disposed in longitudinally extending bores 328a and 328b. Compression spring 330 is disposed around tensioning member 327b and within partial bores 335 and 337 in the adjacent articulating elements. Other compression springs, for example spring 338, are likewise disposed between other articulating elements and each spring may have a different spring rate, i.e., the amount of force required to compress the spring. Elastomeric jacket 355 is shown in phantom view.

The operation of a retractor incorporating variform member 312 will follow the procedures described above in connection with retractors 5 and 10. The variform member 312 differs from the previously described embodiments in that member 312 sequentially deforms between the primary and secondary positions in a predetermined manner. Since each spring, for example 330 and 338, may have a different spring rate, as tensioning member 327b is pulled proximally to deform variform member 312 to the secondary shape from the primary shape, the weakest rate spring will compress first and the strongest rate spring will compress last. Thus, it is possible to provide a "sequential" deforming structure with certain elements of variform member 312 or certain regions of member 312 deforming in sequence. Such sequential deforming may be useful for deforming a variform intraluminal member in a restricted space. For example, referring to fundus retractor 10 in FIGS. 10–13, it may be useful to provide intraluminal member 112 with a sequential deformation in which tip 129 and termination region 138 deform last to wrap the distal end 114 of the member around axis 116 (see FIG. 10).

FIGS. 17–18, 19A and 19B depict a partial sectional view of an alternative embodiment of a variform intraluminal member 412 which differs from esophagus retractor 5 only in construction of the articulating elements in intraluminal member 412. The cooperating articulating elements are made of plastic or other suitable material, for example elements 421 and 422, and are adapted for partially telescoping or nesting with one another to add rigidity to member 412 in the rigid articulated or secondary shape shown in FIG. 17. The primary shape is shown in phantom view in FIG. 17. Articulating element 421 with male protruding form 425a is configured to mate with adjacent articulating member 422 and its female receiving form 425b. The adjacent articulating members may be deformed between the secondary shape and the linear 15 flexible primary shape by singular tensioning member 427 that extends longitudinally through bore 428 and is tensioned in the manner hereinbefore described with handle 35. FIG. 18 depicts a transverse sectional view through protruding form 425a and receiving form 425b in the secondary position. It will be noted that the mating male and female forms in sectional view are non-round or "keyed" to maintain the desired radial angular registration between adjacent elements 421 and 422 in order to maintain the secondary shape.

A unitary sequential deforming structure may be incorporated into variform member 412 and is illustrated in FIGS. 19A–19B in connection with articulating elements 429 and 430. Articulating element 429 is made of a resilient molded plastic, and has a substantially rigid male protruding form 435a (see FIG. 17). The female receiving form 435b of element 430 (see FIG. 17) has a somewhat thin wall section and is molded of resilient plastic in an "out-of-round" or mis-shapened cross-section in its repose state with respect to cooperating male form 435a as shown in FIG. 19A. Thus, when tensioning member 427 is tensioned to press male form 435a into female form 435b, the axial forces on male form 435a must overcome the resilient spring-like forces within the mis-shapened female form 435a to re-shape said female form to accommodate the male form, as depicted in FIG. 19B. By varying the types and densities of plastic in the female form 435b in its repose state, the spring-like resilient forces integral to each articulating element can be varied. Thus, it can be appreciated that such varied rates spring-like resilience in female forms in different articulating elements can be utilized as a means of sequencing the deformation of member 412 between the primary and secondary shapes. It should be appreciated that variform member 412 alternatively could be provided with compression springs disposed around tension member 427 to provide sequential deforming means and be within the scope of the present invention.

From the foregoing it can be seen that there is provided an instrument and method that will greatly facilitate surgical procedures, particularly endoscopic procedures, by allowing the retracting of the esophagus and fundus by intraluminal manipulation from a proximal location. The above-described esophagus retractor additionally may be utilized to facilitate a thoracoscopic truncal vagotomy, an esophageal myotomy, or a sympathectomy. The fundus retractor also may be utilized in a Guarner partial fundoplication as well as other variations of gastric wrap procedures. It can be readily seen that the instrument of the present invention can be manufactured with other specialized shapes, diameters and embodiments to intraluminally retract or reposition other anatomic structures having a lumen, for example the trachea, the bronchial passages or the colon. Alternative embodiments in very small diameters may be used to intraluminally retract structures such as veins and arteries. It should be appreciated that an intraluminal retractor for such applications may range in diameter from 1 millimeter or less to 40 millimeters or more and have any required length to accomplish a particular retraction.

This disclosure is illustrative and not limiting; further variations will be apparent to one skilled in the art in light of this disclosure and are intended to fall within the scope of the appended claims.

I claim:

1. A method for rotationally plicating the fundus of a patient, comprising the steps of:
    engaging a distal portion of an elongate member about a gastroesophageal junction of the patient, wherein a proximal portion of said elongate member extends outwardly through the esophagus of the patient; and rotating said proximal portion of said elongate member about its proximal axis to plicate and wrap the fundus around the esophagus near the esophageal junction.

2. The method of claim 1, wherein the engaging step comprises the steps of:

introducing said elongate member through the patient's esophagus into the patient's stomach; and deforming said distal portion while in the patient's stomach to form a loop which curves around and above the gastroesophageal junction.

3. The method of claim 2, wherein the loop turns in a range of 200° to 360° with a radius in a range of 10 mm to 25 mm.

4. The method of claim 3, wherein the loop is skewed by an angle in a range of 5° to 40° to provide a gap in a range of 5 mm to 30 mm.

5. A method for rotationally plicating a fundus of a patient comprising the steps of:

introducing a distal portion of an elongate member through the patient's mouth and into the patient's stomach in a substantially linear shape;

deforming said distal portion to provide a curved portion of said elongate member which conforms to the patient's gastroesophageal junction and disposing said curved portion around said gastroesophageal junction; and rotating the elongate member about its proximal axis to plicate and wrap the patient's fundus around the esophagus near a region of the gastroesophageal junction.

6. The method of claim 5, further comprising the steps of:

viewing the interior of the patient's stomach through a lumen associated with said elongate member; and selecting a portion of the wall of the fundus for engaging with a projecting distal tip portion on said elongate member prior to the rotating step.

7. The method of claim 5, further comprising the steps of:

placing at least one sleeve through an abdominal wall of the patient;

disposing an endoscope in the sleeve; and viewing through the endoscope a region of the fundus and the gastroesophageal junction while rotating said elongate member.

8. The method of claim 5, further comprising the steps of:

transmitting light from a projecting distal tip portion of said elongate member, thereby illuminating a portion of the wall of the fundus; and observing endoscopically the illuminated portion of the wall of the fundus from the exterior of the fundus.

9. The method of claim 5, further comprising prior to the deforming step, the steps of:

inflating a structure supported by said elongate member; and lifting proximally said elongate member, thereby causing the inflated structure to abut the gastroesophageal junction.

10. The method as in claim 5, further comprising the step of engaging a distal tip on said elongate member against a wall of the fundus above the gastroesophageal junction after the deforming and disposing step and prior to the rotating step.

11. A method for rotationally plicating a fundus of a patient's stomach circumferentially around the patient's esophagus, utilizing an elongate member having a proximal handle portion and a distal portion, comprising the steps of:

introducing said distal portion of said elongate member through the patient's esophagus and into the patient's stomach;

manipulating the handle portion of said elongate member disposed outside the patient's mouth to deform said distal portion into a loop-shaped curvature;

positioning said elongate member so that a lowermost curve of said loop-shaped curvature curves around the gastroesophageal junction of the patient;

pressing into an interior wall of the fundus a distal tip of said elongate member together with a portion of an uppermost curve of said loop-shaped curvature, thereby engaging the fundus;

rotating said handle portion, thereby plicating and wrapping the fundus around the esophagus near the gastroesophageal junction to a circumferentially plicated position;

and securing the fundus in said circumferentially plicated position around the gastroesophageal junction.

12. The method of claim 11, wherein the rotating step further comprises the step of engaging the fundus with said distal tip and uppermost curve of said loop-shaped curvature in a slipping manner, thereby selectively engaging for circumferential plication a portion of the fundus least resistant to plication.

13. The method of claim 11, further comprising prior to the introducing step, the steps of:

disposing an endoscope through an abdominal wall of the patient; and contemporaneous with subsequent steps, viewing the circumferential plication through the endoscope.

14. The method of claim 13, further comprising contemporaneous with the pressing and rotating steps, the steps of:

transmitting light to said distal tip through said elongate member, thereby illuminating a wall portion of the fundus;

observing endoscopically the exterior of the fundus; and positioning said distal tip within the wall of the fundus by the illumination of the wall portion.

15. The method of claim 11, further comprising prior to the articulating step, the steps of:

inflating a balloon incorporated into a medial portion of said elongate member; and lifting proximally said elongate member, thereby causing said balloon to abut the gastroesophageal junction for positioning said loop-shaped curvature in relation to the gastroesophageal junction.

16. The method claim 11, wherein the manipulating step includes the step of sequentially deforming said uppermost and lowermost curves of said loop-shaped curvature, thereby the distal portion may be deformed within the patient's stomach.

17. The method of claim 11, wherein the distal portion of the elongate member is deformed to reach around and above the gastroesophageal junction, thereby to exert force on the fundus as said elongate member is rotated.

* * * * *